United States Patent [19]

Le et al.

[11] Patent Number: 5,264,635

[45] Date of Patent: Nov. 23, 1993

[54] SELECTIVE CRACKING AND ETHERIFICATION OF OLEFINS

[75] Inventors: Quang N. Le, Cherry Hill; Robert T. Thomson, Voorhees, both of N.J.

[73] Assignee: Mobil Oil Corporation, Fairfax, Va.

[21] Appl. No.: 770,215

[22] Filed: Oct. 3, 1991

[51] Int. Cl.$^5$ .................. C07C 41/00; C07C 4/06
[52] U.S. Cl. .................. 568/697; 585/310; 585/324; 585/643
[58] Field of Search .......... 585/310, 324, 648, 651, 585/643; 568/697

[56] References Cited

U.S. PATENT DOCUMENTS 4,969,987 11/1990 Le et al. ................ 208/67

Primary Examiner—Asok Pal
Assistant Examiner—P. Achutamurthy
Attorney, Agent, or Firm—Alexander J. McKillop; Malcolm D. Keen; L. G. Wise

[57] ABSTRACT

A selective alkene upgrading process wherein a mixture of intermediate molecular weight monoalkenes comprising at least one linear alkene component and at least one tertiary alkene component is contacted under selective olefin interconversion conditions with medium pore, shape selective acid catalyst, such as MCM-22 aluminosilicate zeolite, thereby converting at a major amount of linear intermediate alkene to lower alkene while leaving tertiary alkene substantially unconverted. In the preferred embodiments, the process interconversion conditions comprise reaction temperature in the range of about 300° C. to 550° C., pressure in the range of 100 kpa to 1000 kPa, thereby selectively converting at least 60% (net) of linear intermediate alkene while converting less than 20% (net) of branched alkene. By etherifying at least a portion of the unconverted tertiary alkene, an oxygenated fuel having enhanced octane rating is obtained. Cracked lower olefins may be recovered for upgrading.

14 Claims, No Drawings

SELECTIVE CRACKING AND ETHERIFICATION OF OLEFINS

BACKGROUND OF THE INVENTION

This invention relates to a process for converting intermediate olefins, e.g., $C_5$–$C_{12}$ linear mono-alkenes, in contact with a shape selective porous zeolite catalyst to provide lower olefins and isoalkene hydrocarbon products, especially propene, butenes and $C_4$–$C_7$ tertiary alkenes.

Restrictions on the lead and aromatics content of gasoline fuels has created demand for improved processes which upgrade olefins to high octane components. One such class of materials is aliphatic tertiary ethers, such as methyl tert-butyl ether (MTBE) and tert-amyl methyl ether (TAME). However, the availability of isobutylene and isoamylene feedstock for these ethers is limited, and processes for making these olefins from readily available feedstocks are sought.

Recent developments in zeolite catalysts and hydrocarbon conversion processes have created interest in utilizing olefinic feedstocks, such as petroleum refinery streams rich in olefins, for the production of $C_4^+$ tertiary olefins. The $C_5$–$C_7$ light naptha range product of FCC operations is rich in normal and branched mono-alkenes.

Shape selective medium pore zeolites have been demonstrated to have catalytic properties for various types of hydrocarbon conversion. It has been discovered that certain zeolites, such as recently developed MCM-22, are effective catalysts for converting these intermediate olefins to propene and lower isoalkenes at high selectivity.

SUMMARY OF THE INVENTION

An improved process has been found for upgrading olefinic feedstock to iso-alkene rich product by shape selective catalysis under partial conversion conditions at elevated temperature and low pressure. The improvement herein comprises selectively converting $C_5+$ linear olefin feedstock containing a mixture of linear and branched olefins to produce propene and butenes by contacting said feedstock with olefin interconversion catalyst composition in a primary fluidized bed catalytic reaction zone under selective linear olefin interconversion conditions to produce propene and butenes; separating effluent from the primary reaction zone to recover a light propene-rich stream and a liquid hydrocarbon stream containing predominantly unconverted branched $C_5+$ olefins; and etherifying the liquid hydrocarbon stream by reacting at least a portion of branched $C_5+$ olefins with a lower alkanol, thereby obtaining oxygenated fuel of enhanced octane rating.

DESCRIPTION OF SPECIFIC EMBODIMENTS

In shape selective zeolite catalysis, at low pressure and high temperature light and intermediate olefins can be interconverted or redistributed to produce olefinic product rich in isoalkenes. At low pressure and high temperature up to about 700° C., thermodynamics restrict the olefin distribution to low molecular weight. This is the basis for olefin interconversion process, i.e., to operate under conditions where linear olefins, such as $C_5$–$C_{12}$ mono-alkenes, can be converted selectively to an equilibrated distribution of olefins with iso-butenes and iso-pentenes maximized.

Various olefinic materials are suitable for use as feedstock in the process of this invention, especially mixtures linear and branched monoalkenes having 5 to 12 carbon atoms. Suitable olefinic feedstocks can be obtained from a variety of sources including fossil fuel processing streams such as fluid catalyst cracking (FCC) of heavy hydrocarbons, coal by-products, and various synthetic fuel processing streams. Olefinic effluent from the fluidized catalytic cracking of gas oil, and the like, is a valuable source of mixed linear and branched olefins, mainly $C_5$–$C_{12}$ olefins, suitable for conversion according to the present olefin interconversion process. Olefinic refinery streams can be advantageously converted to valuable higher hydrocarbons employing the catalytic interconversion process of this invention.

The olefin interconversion process as utilized in the present invention can use fixed bed, moving bed or fluid bed reactors containing shape selective catalyst, such as MCM-22 zeolite or mixtures thereof with other shape selective catalysts, such as ZSM-5. Typical operating conditions encompass temperatures between 300° and 550° C., low pressure, generally between 100 and 1000 kPa, and high space velocity. Catalyst acidity can also be a factor in the reaction. It is preferred to maintain the acid activity (alpha value) of MCM-22 in the range of about 1 to 150, preferably less than 50, and most preferably less than 10.

Olefin upgrading has been improved by use of MCM-22 zeolite as a catalyst for interconversion of olefin, such as n-pentenes, n-hexenes, etc. to higher value products, viz., isobutylene and isoamylenes. MCM-22 olefin interconversion catalysis is also characterized by low yields of undesirable normal C3–C5 alkanes. The process is preferably carried out at relatively low pressure (less than about 700 kpa) and high temperature (typically greater than about 300° C.) to maximize $C_4+C_5$ tertiary olefin yields. While the process can be carried out in either a fixed or a fluid-bed mode, the latter is preferred due to the relatively rapid catalyst aging.

Particle size distribution is known to be a significant factor in achieving overall homogeneity in turbulent regime fluidization. It is desired to operate catalytic processes with particles that will mix well throughout the bed. Large particles (Geldart type B or C) having a particle size greater than about 1000 microns can be fluidized with difficulty, and it is customary in catalysis to employ a finely divided particles having size range of about 5 to 100 microns. Average particle size for a dense bed or turbulent regime bed is usually about 20 to less than 100 microns, preferably 40 to 80 microns. Homogeneous particle distribution in the bed can be enhanced by having a mixture of larger and smaller particles within the operative range, and it is particularly desirable to have a significant amount of fines. Close control of distribution can be maintained to keep a portion of the total catalyst in the fluidization zone in the size range less than 40 microns. This class of fluidizable particles is classified as Geldart Group A. Accordingly, the fluidization regime is controlled to assure operation between the transition velocity and transport velocity. Fluidization conditions are substantially different from those found in slugging, non-turbulent dense beds or conventional transport beds.

Under optimized process conditions the turbulent bed has a superficial vapor velocity of about 0.3 to 2 meters per second (m/sec). At higher velocities entrainment of fine particles may become excessive. At lower velocities, the formation of large bubbles or gas voids can be detrimental to process utilization, eg- chemical conversion, mass or thermal transfer, etc.

A convenient measure of turbulent fluidization is the bed density. A typical turbulent bed has an operating density of about 100 to 500 kg/m$^3$, preferrably about 300 to 500 kg/m$^3$, measured at the bottom of the reaction zone, becoming less dense toward the top of the reaction zone, due to pressure drop and particle size differentiation. This density is generally between the catalyst concentration employed in dense beds and the dispersed transport systems. Pressure differential between two vertically spaced points in the reactor column can be measured to obtain the average bed density at such portion of the reaction zone. For instance, in a fluidized bed system employing zeotite fine particles having an apparent packed density of 750 kg/m$^3$ and real density of 2430 kg/m$^3$, an average fluidized bed density of about 300 to 500 kg/m$^3$ is satisfactory.

By virtue of the turbulence experienced in the turbulent regime, gas-solid contact in the catalytic reactor is improved, providing substantially complete conversion, enhanced reaction selectivity and temperature uniformity. One main advantage of this technique is the inherent control of bubble size and characteristic bubble lifetime. Bubbles of the gaseous reaction mixture are small, random and short-lived, thus resulting in good contact between the gaseous reactants and the solid catalyst particles.

The weight hourly space velocity and uniform contact provides a close control of contact time between vapor and solid phases, typically about 1 to 10 seconds. Another advantage of operating in such a mode is the control of bubble size and life span, thus avoiding large scale gas by-passing (slugging) in the reactor.

As the superficial gas velocity is increased in the dense bed, eventually slugging conditions occur and with a further increase in the superficial gas velocity the slug flow breaks down into a turbulent regime. The transition velocity at which this turbulent regime occurs appears to decrease with particle size. (see Avidan et al. in U.S. Pat. Nos. 4,746,762 and 4,547,616). As the large particle transport velocity is approached, there is a sharp increase in the rate of particle carryover, and in the absence of solid particle recycle, the bed could empty quickly.

Several useful parameters contribute to fluidization in the turbulent regime in accordance with the process of the present invention. When employing a ZSM-5 type zeolite catalyst in fine powder form such a catalyst should comprise the zeolite suitably bound or impregnated on a suitable support with a solid density (weight of a representative individual particle divided by its apparent "outside" volume) in the range from 0.6-2 g/cc, preferably 0.9-1.6 g/cc. The catalyst particles can be in a wide range of particle sizes up to about 250 microns, with an average particle size between about 20 and 100 microns, preferably in the range of 10-150 microns and with the average particle size between 40 and 80 microns. When these solid particles are placed in a fluidized bed where the superficial fluid velocity is 0.3-2, operation in the turbulent regime is obtained. The velocity specified here is for an operation at a total reactor pressure of about 100 to 300 kPa. Those skilled in the art will appreciate that at higher pressures, a lower gas velocity may be employed to ensure operation in the turbulent fluidization regime.

The reactor can assume any technically feasible configuration, but several important criteria should be considered. The bed of catalyst in the reactor can be at least about 5-20 meters in height, preferably about 9 meters. Fine particles may be included in the bed, especially due to attrition, and the fines may be entrained in the product gas stream. A typical turbulent bed may have a catalyst carryover rate up to about 1.5 times the reaction zone inventory per hour. If the fraction of fines becomes large, a portion of the carryover can be removed from the system and replaced by larger particles. It is feasible to have a fine particle separator, such as a cyclone and/or filter means, disposed within or outside the reactor shell to recover catalyst carryover and return this fraction continuously to the bottom of the reaction zone for recirculation at a rate of about one catalyst inventory per hour. Optionally, fine particles carried from the reactor vessel entrained with effluent gas can be recovered by a high operating temperature sintered metal filter.

Careful selection of catalyst components to optimize C3-C4 and isoalkene selectivity is important to overall success of the process. The catalyst may consist essentially of MCM-22 aluminosilicate zeolite, having an acid cracking activity less than 15 (standard alpha value) and moderately low constraint index (C.I. = 1.5). The moderately constrained medium pore zeolite has a pore size of about 5-8Å, able to accept linear olefin components found in most FCC naphtha may be used, it is advantageous to employ standard MCM-22, suitably modified if desired to adjust acidity. A typical zeolite catalyst component having Bronsted acid sites may consist essentially of aluminosilicate zeolite with 5 to 95 wt. % silica and/or alumina binder.

Usually the zeolite crystals have a crystal size from about 0.01 to 2 microns or more. In order to obtain the desired particle size for fluidization in the turbulent regime, the zeolite catalyst crystals are bound with a suitable inorganic oxide, such as silica, alumina, etc. to provide a zeolite concentration of about 5 to 95 wt %.

In selective olefin disproportionation reactions, it is advantageous to employ a standard zeolite having a silica:alumina molar ratio of 25:1 or greater in a once-through fluidized bed unit to convert about 5 to 50 weight percent, preferably about 10-30 wt %, of the C5-C12 feedstock hydrocarbons in a single pass. Particle size distribution can be a significant factor in transport fluidization and in achieving overall homogeneity in dense bed, turbulent regime or transport fluidization. It is desired to operate the process with particles that will mix well throughout the bed. It is advantageous to employ a particle size range consisting essentially of 1 to 150 microns. Average particle size is usually about 20 to 100 microns.

In the present invention MCM-22, a new zeolite which has been found to be active for a wide variety of hydrocarbon conversions, is shown to have high activity and selectivity for the selective conversion of naphtha-range olefinic C5-C12 hydrocarbons to higher value $C_3$-$C_5$ linear and iso-olefins. Synthesis of MCM-22 is disclosed in U.S. Pat. No. 4,954,325 (Rubin et al.), incorporated by reference. MCM-22 appears to be related to the composition named "PSH-3" described in U.S. Pat. No. 4,439,409. Zeolite MCM-22 does not appear to contain all the components apparently present in the PSH-3 compositions. Pure zeolite MCM-22 is not contaminated with other crystal structures, such as ZSM-12 or ZSM-5, and exhibits unusual sorption capacities and unique catalytic utility when compared to the PSH-3 compositions.

Zeolite MCM-22 has a composition involving the molar relationship:

$$X_2O_3:(n)YO_2.$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2;$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits high surface area greater than 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations. It can, therefore, be used as an olefin interconversion catalyst with acid activity without an exchange step. To the extent desired, however, the original sodium cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the activity of the catalyst for olefin interconversion. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has a defined X-ray diffraction pattern.

Prior to its use as olefin interconversion catalyst, the MCM-22 crystals should be subjected to thermal treatment to remove part or all of any organic constituent present therein. Zeolite MCM-22, especially in its metal, hydrogen and ammonium forms, can be beneficially converted to another form by thermal treatment at a temperature of at least about 370° C. The stability of the catalyst of this invention may be increased by steaming, as described in U.S. Pat. Nos. 4,663,492.

In order to more fully illustrate the olefin conversion process of this invention and the manner of practicing same, the following examples are presented.

Zeolite Synthesis: MCM-22 is prepared by adding 4.49 parts quantity of hexamethyleneimine to a mixture containing 1.00 part sodium aluminate, 1.00 part 50% NaOH, 8.54 parts Ultrasil VN3 and 44.19 parts deionized $H_2O$. The reaction mixture was heated to 143° C. (290° F.) and stirred in an autoclave at that temperature for crystallization. After full crystallinity was achieved, the majority of the hexamethyleneimine was removed from the autoclave by controlled distillation and the zeolite crystals separated from the remaining liquid by filtration, washed with deionized $H_2O$ and dried. The zeolite was then calcined in nitrogen at 540° C., exchanged with an aqueous solution of ammonium nitrate and calcined in air at 540° C. The zeolite was tabletted, crushed and sized to 30/40 mesh.

The MCM-22 catalyst had the following properties:

| | |
|---|---|
| Surface Area (BET), m²/g | 503 |
| $SiO_2/Al_2O_3$ (molar) | 27 |
| Na, ppm | 495 |
| Alpha | 693 |
| Sorption Properties, wt. % | |
| $H_2O$ | 15.0 |
| $CyC_6$ | 12.5 |
| $n-C_6$ | 16.0 |
| Ash at 1000° C., wt. % | 99.05 |

PROCESS EXAMPLE A

Selective olefin conversion reactions are demonstrated to show selectivity in producing lower olefins and isoalkenes. This example of FCC gasoline cracking is performed in a nontransport regime fluid bed reactor using steamed MCM-22/silica-alumina clay catalyst (25 wt % zeolite, 4 alpha), prepared according the above procedure. In the reactor, catalyst is heated to 425° C. under nitrogen and maintained at this temperature and 200 kPa (15 psig) for one hour. To commence the reaction, light FCC gasoline ($C_5$-102° C.) is charged to the reactor at a rate of 1.7 parts by weight feed/part total catalyst-hour (6.8 WHSV). Nitrogen is cofed to the reactor to insure proper fluidization of the catalyst in the turbulent regime. Feedstock is fed to the reactor for 3 hours, followed by 60 minutes of nitrogen stripping. The entire reactor effluent from the feed and stripping periods is collected and analyzed by gas chromatography.

The results from studies of FCC gasoline cracking over MCM-22, displayed in Table A, show that over 60% of the linear isomers in the feedstream are converted to lighter products, which are primarily $C_3$-$C_4$ olefins. The selective nature of the linear olefin cracking is evident since the conversion levels for all other $C_5^+$ components are significantly lower.

TABLE A

The Cracking of Light FCC Gasoline To Light Olefins over MCM-22

| Composition, wt % | Feed | Product | Net Conv. |
|---|---|---|---|
| Light Gas ($C_1$-$C_2$) | 0.0 | 1.0 | |
| $C_3$-$C_4$ Paraffins | 1.6 | 4.6 | |
| $C_3$-$C_4$ Olefins total | 3.1 | 17.6 | |
| $C_5$-$C_6$ Paraffins | 26.7 | 25.7 | 3.7% |
| Linear $C_5$-$C_6$ Olefins | 14.1 | 5.6 | 60.3% |
| Branched $C_5$-$C_6$ Olefins | 20.7 | 16.8 | 18.8% |
| Other $C_6$ (Cyclics, etc.) | 8.7 | 6.9 | 20.7% |
| Total $C_7^+$ | 25.2 | 22.1 | 12.3% |

The reaction effluent may be separated to recover one or more light olefinic streams, such as a $C_4-$ stream or an olefinic product stream rich in $C_4$-$C_5$ tertiary olefins, which may be converted to MTBE and/or TAME. A heavy hydrocarbon stream rich in branched olefins is be recovered for further conversion by etherification. It as feasible to recover propene and butenes as a product stream, with a $C_5+$ stream rich in tertiary olefins being partially etherified as a gasoline blending component. It is understood that unreacted branched aliphatics in the feedstock enhance the octane value of the gasoline for blending.

The reaction path to the desired tertiary olefin product may proceed by isomerization (skeletal and/or bond) as well as cracking and oligomerization. However, these data clearly show a preferential net conversion of linear olefin to tertiary olefin.

Etherification—The reaction of methanol with isobutylene and isoamylenes at moderate conditions with a resin catalyst is known technology. Processes for producing and recovering MTBE, TAME and other methyl tert-alkyl ethers for $C_4$-$C_7$ iso-olefins are known to those skilled in the art, such as disclosed in U.S. Pat. Nos. 4,788,365; 4,969,987; and 5,015,782 and applications 07/607932 and 07/612932 (Le, Owen et al.), incorporated by reference.

PROCESS EXAMPLE B

The olefinic C5- product of Example A is etherified by reaction with methanol over acid catalyst to produce tertiary amyl, hexyl and heptyl ether octane improvers. FCC gasoline etherification is performed in a fixed bed reactor, using zirconia-bound zeolite beta catalyst. Catalyst is heated to 400° F. at 400 psig under nitrogen and maintained under these conditions for 16 hours, after which time the temperature is decreased to 200° F. The hydrocarbon feed is blended with methanol (75 wt. % hydrocarbon/25 wt. % absolute alcohol) and charged at a rate of 3.0 grams of liquid per gram of zeolite per hour. The total liquid product is washed with water to remove unreacted methanol from the hydrocarbons. The $C_4^-$ and $C_5$ paraffin concentrations decrease, probably due to evaporative losses.

TABLE B

| Etherification of Gasoline Branched Olefins Over Zeolite Beta | |
|---|---|
| | Reaction Product |
| Temperature | 93° C./200° F. |
| Pressure | 2850 kPa/400 psig |
| Total Feed Rate, WHSV | 3.0 |
| Composition, wt. % | |
| Total $C_4^-$ | 2.7 |
| Branched $C_5$ Olefins | 4.6 |
| Linear $C_5$ Olefins | 8.2 |
| $C_5$ Paraffins, Others | 15.2 |
| Branched $C_6$ Olefins | 8.4 |
| Linear $C_6$ Olefins | 6.0 |
| $C_6$ Paraffins, Others | 19.8 |
| Total $C_7^+$ | 25.8 |
| Methyl $C_5$ Ether (TAME) | 5.0 |
| Methyl $C_6$ Ethers | 2.6 |
| Methyl $C_7$ Ethers | 1.7 |

In addition to the above examples, the selective removal of linear olefins in hydrocarbon streams may potentially be performed in many other reactor configurations; however, fluidized bed configuration is preferred, particularly at high temperature (350°-550° C.) and short-contact time (<10 sec) conditions. Moving-bed and fixed-bed reactors are also viable for high activity and stable catalysts which might not require frequent regeneration. Preferred process conditions for fixed and moving -bed configuration would be in lower reactor temperature, space velocities (0.1-10 WHSV) and in the substantial absence of added hydrogen.

In addition to FCC gasolines, other potential olefinic feedstocks include coker naphtha, dehydrogenated naphtha, dehydrogenated Udex raffinate, and olefin oligomers. Typical olefinic feedstock materials for selective upgrading are produced in petroleum refineries by distillation of FCC reaction effluent. Typical FCC naphtha feedstock usually contain 15 to 50 wt. % C5-C12 normal and branched alkanes, C6+ cycloaliphatic (i.e., naphthene) hydrocarbons, and 1 to 40% aromatics. The C5-C12 hydrocarbons have a normal boiling range up to 175° C. In addition to FCC naphtha, the process can utilize various feedstocks, such as derived from hydrocracking, heavy FCC naphtha, hydrocracked naphtha, coker naphtha, visbreaker naphtha and mixtures thereof. For purposes of explaining the invention, discussion is directly mainly to FCC light naphtha materials.

The selective cracking of linear olefins over MCM-22 may provide an attractive route for the upgrading of hydrocarbon streams, including FCC gasoline. The light hydrocarbon products (propylene and butenes) as well as unreacted $C_5^+$ branched olefins can be used as feedstocks for the production of "clean fuels" such as ethers and alkylate. The C3-C4 normal and isoalkenes can be upgraded to high octane fuel components by conventional alkylation or etherification.

If proposed regulations on the minimum oxygen content and maximum olefin concentration in the gasoline pool are mandated, it would be desirable to preferentially remove the linear olefins from FCC gasoline and thus increase the concentration of unconverted branched olefins, which may be recovered from reaction effluent and converted to ethers. The production of $C_4^-$ olefins from the cracking reaction is an additional benefit since these hydrocarbons are used in downstream processes, such as alkylation and etherification, to produce other "clean fuel" components.

Selective removal of linear olefins from mixed hydrocarbon streams has many potential applications, including the production of "clean fuels." The catalytic cracking of gas oil (FCC) produces, among other products, large volumes of gasoline-range hydrocarbons. However, for environmental reasons, replacement of the highly olefinic FCC product with high octane ethers and alkylate in the gasoline pool would be highly desirable. Since these latter components are produced from feedstocks such as propylene, butenes, and branched $C_5$-$C_7$ olefins, it would be beneficial to selectively crack linear olefins in FCC gasoline to $C_3$-$C_4$ olefinic products. Therefore, development of a process to accomplish this selective conversion would be highly desirable.

The cracking of FCC gasoline would be performed in a reactor located downstream of the FCC unit. The $C_4^-$ product stream from the gasoline cracking process could be sent to the FCC unsaturated gas plant, with branched $C_5^+$ olefins possibly being etherified with methanol to increase the oxygen content of the gasoline pool.

Various modifications can be made to the system, especially in the choice of equipment and non-critical processing steps. While the invention has been described by specific examples, there is no intent to limit the inventive concept as set forth in the following claims.

We claim:

1. A process for selectively converting $C_5^+$ linear olefin feedstock containing a mixture of linear and branched olefins to produce propene and butenes, which comprises contacting said feedstock with olefin interconversion catalyst composition in a primary fluidized bed catalytic reaction zone under selective linear olefin interconversion conditions to produce propene and butenes;

separating effluent from the primary reaction zone to recover a light propene-rich stream and a liquid hydrocarbon stream containing predominantly unconverted branched $C_5+$ olefins; and etherifying the liquid hydrocarbon stream by reacting at least a portion of branched $C_{5+}$ olefins with a lower alkanol, thereby obtaining oxygenated fuel of enhanced octane rating.

2. The process of claim 1 wherein the catalyst comprises crystalline material having a composition comprising the molar relationship:

$$X_2O_3:(n)YO_2.$$

wherein n is at least about 10, X is a trivalent element and Y is a tetravalent element.

3. The process of claim 2 wherein X is selected from the group consisting of aluminum, boron, gallium and combinations thereof and Y is selected from the group consisting of silicon, germanium and combinations thereof.

4. The process of claim 3 wherein X comprises aluminum and Y comprises silicon.

5. The process of claim 1 wherein the olefin has 5 to 12 carbon atoms.

6. The process of claim 1 wherein the primary zone reaction conditions include a temperature greater than 300° C., a pressure less than 1000 kpa and an weight hourly space velocity (WHSV) of from about 1 to 50 $hr^{-1}$.

7. The process of claim 1 wherein the reaction conditions include a temperature of from about 300° to 550° C. a pressure of about 100 to 1500 kpa and an weight hourly space velocity (WHSV) of from about 2 to 20 $hr^{-1}$.

8. The process of claim 1 wherein reaction effluent is separated to recover an olefinic product stream rich in $C_4-C_5$ tertiary olefins and wherein a $C_6+$ liquid hydrocarbon is recovered.

9. The process of claim 1 wherein the catalyst consists essentially of borosilicate MCM-22 having an alpha value acid activity less than 10, based on active catalyst solids.

10. In the process for upgrading linear and branched $C_5-C_{12}$ olefin feedstock to iso-alkene rich product by shape selective catalysis at elevated temperature and low pressure, the improvement which comprises: reacting the olefin feedstock in contact with MCM-22 zeolite catalyst under reaction conditions sufficient to provide increased yield of isobutene and isopentene; and further reacting at least a portion of isobutene, isopentene and branched heavier olefin by etherification with a lower alkanol.

11. A selective alkene upgrading process wherein a mixture of $C_5-C_{12}$ range intermediate molecular weight monoalkenes comprising at least one linear alkene component and at least one tertiary alkene component is contacted under selective olefin interconversion conditions with medium pore, shape selective acid metallosilicate catalyst having the structure of MCM-22 zeolite, thereby converting a major amount of linear intermediate alkene to lower alkene while leaving tertiary alkene substantially unconverted; and etherifying at least a portion of said unconverted tertiary alkene.

12. The process of claim 11 wherein said olefin interconversion conditions comprise reaction temperature in the range of about 300° C. to 550° C.; pressure in the range of 100 kpa to 1000 kpa, and wherein selective interconversion of the linear unsaturated component produces lower alkenes without substantial reaction of said tertiary alkene component.

13. A selective alkene upgrading process wherein a feedstock mixture of $C_5-C_{12}$ range intermediate molecular weight monoalkenes comprising at least one linear alkene component and at least one tertiary alkene component is contacted under selective olefin interconversion conditions with medium pore, shape selective acid metallosilicate catalyst having the structure of MCM-22 zeolite, thereby selectively converting at least 60% (net) of linear intermediate alkene and converting less than 20% (net) of branched alkene; said olefin interconversion conditions comprising reaction temperature in the range of about 300° C. to 550° C.; pressure in the range of 100 kpa to 1000 kpa; and etherifying at least a portion of unconverted branched alkene by reaction with lower alkanol to produce tertiary ether.

14. The process of claim 13 wherein the feedstock mixture consists essentially of light FCC gasoline rich in $C_5-C_7$ alkenes.

* * * * *

UNITED STATES PATENT AND TRADEMARK OFFICE
CERTIFICATE OF CORRECTION

PATENT NO. : 5,264,635

DATED : November 23, 1993

INVENTOR(S) : Q. N. Le and R. T. Thomson

It is certified that error appears in the above-identified patent and that said Letters Patent is hereby corrected as shown below:

Col. 10, line 31, "tertiary" should be --branched--

Signed and Sealed this

Twenty-first Day of June, 1994

Attest:

BRUCE LEHMAN

Attesting Officer      Commissioner of Patents and Trademarks